(12) United States Patent
Andreacchi

(10) Patent No.: US 8,734,891 B2
(45) Date of Patent: May 27, 2014

(54) METHOD FOR SELECTIVE COATING OF ENDOLUMINAL PROSTHESES

(75) Inventor: Anthony S. Andreacchi, San Jose, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 73 days.

(21) Appl. No.: 13/611,663

(22) Filed: Sep. 12, 2012

(65) Prior Publication Data

US 2013/0011545 A1 Jan. 10, 2013

Related U.S. Application Data

(62) Division of application No. 12/145,141, filed on Jun. 24, 2008, now Pat. No. 8,282,981.

(51) Int. Cl.
*A61L 33/00* (2006.01)
*B05D 3/00* (2006.01)
*B05C 13/00* (2006.01)

(52) U.S. Cl.
USPC .................. 427/2.24; 427/2.25; 118/500

(58) Field of Classification Search
USPC .................. 427/2.24, 2.25; 118/500
See application file for complete search history.

(56) References Cited

U.S. PATENT DOCUMENTS

| 7,563,324 B1 | 7/2009 | Chen et al. |
| 7,892,592 B1 | 2/2011 | Chen et al. |
| 8,282,981 B2 | 10/2012 | Andreacchi |
| 2005/0074544 A1 | 4/2005 | Pacetti et al. |
| 2007/0141232 A1 | 6/2007 | Tochterman et al. |

OTHER PUBLICATIONS

W. R. Beam, "Application of coatings to substrates by capillary action", IBM Technical Disclosure Bulletin, vol. 8, No. 11, p. 1468 (1966).

*Primary Examiner* — Bijan Ahvazi
*Assistant Examiner* — Atnaf Admasu
(74) *Attorney, Agent, or Firm* — Squire Sanders (US) LLP

(57) ABSTRACT

A system and method for coating an endoprosthesis involves an applicator capable of delivering a coating substance to the endoprosthesis without spraying. The applicator may have a tube or die through which a coating substance is moved upwards by capillary action or by means of a pump so as to form an accumulation of the coating substance at an upper portion of the applicator. The endoprosthesis can be lowered onto the accumulation, then axially translated or rotated in order to transfer the coating substance to selected portions of the endoprosthesis. The applicator is lowered and/or the endoprosthesis is raised in order to form gaps in the coating. Selective coating of abluminal or luminal surface of the endoprosthesis may also be performed by allowing the surface to skip on a liquid surface of a pool of the coating substance.

13 Claims, 6 Drawing Sheets

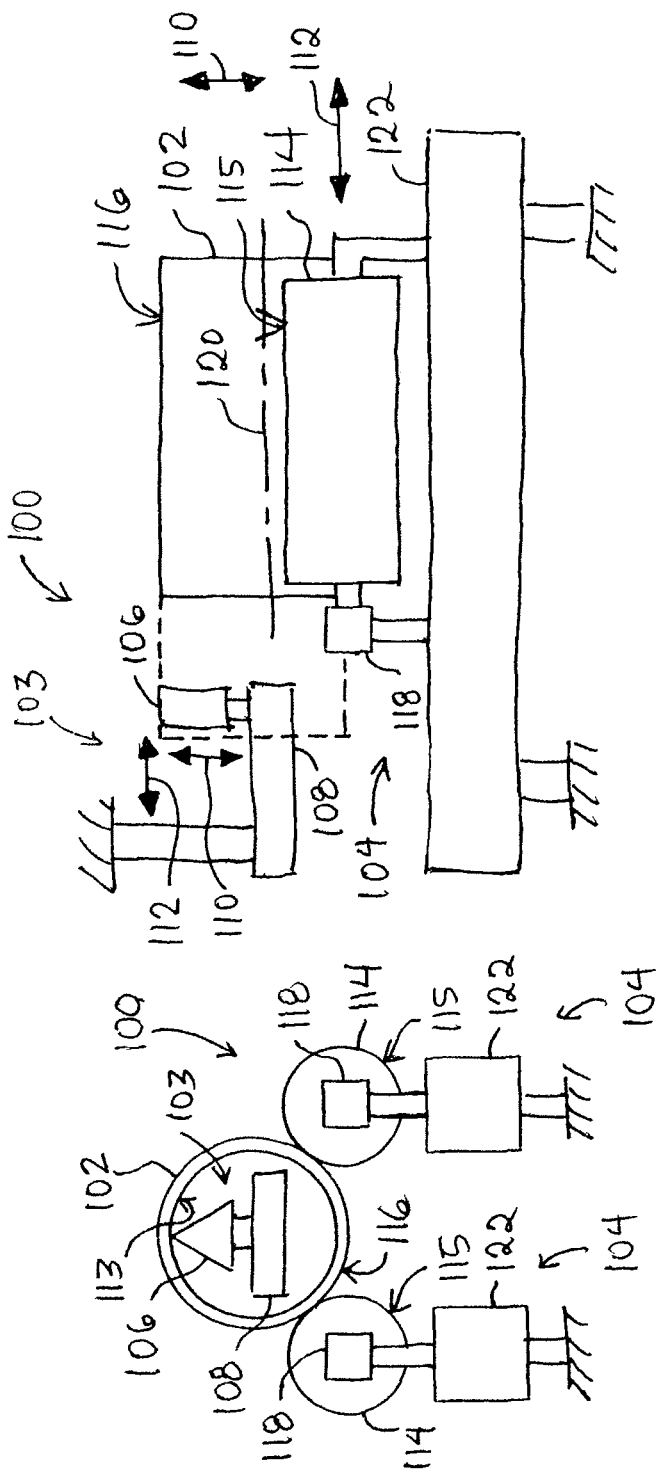

_US 8,734,891 B2_

METHOD FOR SELECTIVE COATING OF ENDOLUMINAL PROSTHESES

CROSS-REFERENCE TO RELATED APPLICATION

This application is a divisional of application Ser. No. 12/145,141, filed Jun. 24, 2008, which is incorporated herein by reference.

BACKGROUND OF THE INVENTION

1. Field of the Invention

This invention relates generally to endoprostheses and, more particularly, to a system and method for coating endoprostheses such as stents.

2. Description of the State of the Art

The present invention involves radially expandable endoluminal prostheses or endoprostheses, which are medical devices adapted to be implanted in an anatomical lumen. An "anatomical lumen" refers to a cavity of a tubular organ such as a blood vessel. A stent is an example of these endoprostheses. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels.

Stents have been made of many materials including metals and polymers. Polymeric materials include both nonbioerodable and bioerodable plastic materials. The cylindrical structure of stents is typically composed of scaffolding that includes a pattern or network of interconnecting structural elements or struts. The scaffolding can be made of a base material that is metallic or polymeric and can be in the form of wires, bars, tubes, or planar films of material rolled into a cylindrical shape.

FIG. 1 shows an endoprosthesis 10 in the form of a stent. The endoprosthesis 10 includes a plurality of ring struts 12 that define a plurality of undulating hoops or rings 14 having an initial diameter. The endoprosthesis 10 can include any number of rings 14 to achieve a desired overall length. The rings 14 are capable of being compressed in a radial direction 16 to a diameter smaller than the initial diameter and are connected to each other by a plurality of connecting struts 18. The rings may also include any number of ring struts 12 to achieve a desired diameter. The endoprosthesis 10 is in the shape of a hollow cylinder or tube (illustrated in broken lines) having a central axis 20. Each ring strut 12 and connecting strut 18 has an outer or abluminal surface 22 that faces away from the central axis 20 and an inner or luminal surface 24 that faces toward the central axis.

Stents are used not only for mechanical intervention but also as vehicles for providing biological therapy. Biological therapy can be achieved by medicating the stents. Medicated stents or drug eluting stents provide for the local administration of a therapeutic substance at the diseased site. In order to provide an efficacious concentration to the treated site, systemic administration of such medication often produces adverse or even toxic side effects for the patient. Local administration is a preferred method of treatment in that smaller total levels of medication are administered in comparison to systemic dosages, but are concentrated at a specific site. Local administration thus produces fewer side effects and achieves more favorable results.

A medicated endoprosthesis may be fabricated by coating the surface of either a metallic or polymeric scaffolding to produce a drug reservoir layer on the surface. The drug reservoir layer typically includes a polymeric carrier that includes an active agent or drug. To fabricate a coating, a polymer, or a blend of polymers, can be applied on the endoprosthesis using commonly used techniques known to those having ordinary skill in the art. A composition or substance to be coated onto the endoprosthesis may include a solvent, a polymer dissolved in the solvent, and an active agent dispersed in the blend. Conventionally, the substance is applied to the endoprosthesis by immersing the endoprosthesis in the substance or by spraying the substance onto the endoprosthesis.

As used here, "endoprosthesis" encompasses devices that are implanted permanently and temporarily inside a human or animal body. Metallic stents are permanently implanted, whereas polymeric stents are usually designed to resorb into the body. Temporarily implanted or non-permanent endoprostheses are removed from the patient after a relatively short indwelling time. Temporarily implanted endoprostheses can be a catheter system, such as a balloon catheter used dilate a constriction within body lumen during angioplasty and a stent delivery system used to position and deploy a stent with a body lumen. Temporarily implanted endoprostheses can be medicated to provide localized delivery of therapeutic or beneficial agents. An outer surface coating can be used as a vehicle to carry the agents.

An endoprosthesis coating should meet several well-known criteria including mechanical integrity, controlled release of the drug, and biocompatibility. A primer layer can serve as a functionally useful intermediary layer between the surface of the device base material and an active agent-containing or reservoir coating, or between multiple layers of reservoir coatings. The primer layer provides an adhesive tie between the reservoir coating and the device base material. Also, a barrier or polymeric topcoat layer above a reservoir layer serves the purpose of controlling the rate of release of an active agent or drug. An endoprosthesis may also include a biobeneficial coating over a reservoir layer and/or topcoat layer to improve the biocompatibility of the coating.

It would be advantageous to reduce the amount of coating material on certain surfaces of an endoprosthesis without adversely impacting the treatment capabilities. For instance, the presence of a topcoat layer, such as a poly(ester amide) (PEA) layer, on a luminal surface can have a detrimental impact on the implantation process and coating mechanical integrity. PEA topcoats can change the coefficient of friction between an endoprosthesis and a delivery device carrying the endoprosthesis to the implantation site. In addition, some PEA polymers have structures that cause them to be sticky or tacky, thereby inhibiting the smooth release of an endoprosthesis from a delivery device. Therefore, it would be desirable to limit the presence of PEA topcoats on the luminal surface.

It may also be advantageous to have an endoprosthesis with an asymmetric coating in which a different therapeutic agent is applied to the abluminal than the luminal surface. For example, an angiogenic substance and/or an anti-thrombotic substance can be applied to the luminal surface which faces flowing blood when the endoprosthesis is implanted in a blood vessel. The angiogenic substances can stimulate or promote formation of one or more collateral vessels downstream of, or distal to, the site of implantation. The collateral vessels facilitate restoration of blood flow to deprived tissue, thereby constituting "natural bypasses" around an occluded vessel. The anti-thrombotic substance can inhibit clogging of the endoprosthesis as a result of interaction between the endoprosthesis and blood flow therethrough. In order to treat restenosis, a substance that inhibits abnormal migration and/ or proliferation of smooth muscle cells can be applied to the abluminal surface which would face the blood vessel walls after implantation.

Conventional methods of loading an endoprosthesis with beneficial agents by either dipping or spraying often require coating the entire endoprosthesis or large portions of the endoprosthesis with the beneficial agent. Additionally, if it is desired to superimpose two or more conventionally-loaded prostheses, such as with nested stents or bifurcated stents, the total dosage of beneficial agent to the lumen may well exceed the nominal or optimal dosage. Another drawback of conventional coating methods is the lack of or difficulty in achieving selective dosing that provides various beneficial agents or various concentrations of the same beneficial agent at different locations on an endoprosthesis.

The features and advantages of the invention will be more readily understood from the following detailed description which should be read in conjunction with the accompanying drawings.

SUMMARY OF THE INVENTION

Briefly and in general terms, the present invention is directed to a method for coating an endoprosthesis.

In aspects of the invention, a method comprises forming the accumulation of a coating substance on an uppermost tip of a fluid conduit, the accumulation extending above the tip. The method further comprises bringing the accumulation on the tip and a portion of an endoprosthesis into contact with each other, the portion of the endoprosthesis located above the accumulation. The method further comprises translating or rotating the endoprosthesis relative to the tip while the accumulation on the tip and the endoprosthesis are in contact with each other, thereby transferring the coating substance from the tip to the endoprosthesis.

In aspects of the invention, a method comprises positioning an applicator and a substrate of an endoprosthesis relative to each other so that the substrate is located above and in contact with a coating substance on the applicator, and moving the substrate relative to the applicator while the substrate is in contact with the coating substance on the applicator so that the coating substance is transferred from the applicator to the substrate.

In other aspects, the applicator does not contact the substrate and the applicator includes a tube for delivering the coating substance to an aperture of the applicator. In other detailed aspects, the method further comprises delivering the coating substance to the aperture of the applicator by capillary action or wicking action.

In other aspects, the applicator includes a vertical tube for delivering the coating substance to an uppermost tip of the applicator, the tube having an outlet at the tip, an inlet below the outlet, and interior surfaces that are closer to each other at the outlet than at the inlet.

In other aspects, the coating substance is carried by the applicator as a pool. When positioning the applicator and the substrate relative to each other, the substrate contacts the pool and does not contact the applicator. Also, when moving the substrate relative to the applicator, the coating substance is transferred from the pool to either one but not both of an abluminal surface and a luminal surface of the endoprosthesis.

The features and advantages of the invention will be more readily understood from the following detailed description which should be read in conjunction with the accompanying drawings.

BRIEF DESCRIPTION OF THE DRAWINGS

The figures are not necessarily drawn to scale, and the relative sizes of structures depicted may have been exaggerated for illustrative purposes.

FIG. 5 is a diagrammatic end view of a system for coating an endoprosthesis, showing a holding assembly engaging an abluminal surface of the endoprosthesis and showing a coating assembly applying a coating substance to a luminal surface of the endoprosthesis.

FIG. 6 is a diagrammatic side view of the system of FIG. 5, showing the endoprosthesis after having been axially translated away from the coating assembly.

DETAILED DESCRIPTION OF THE INVENTION

Figure 1:
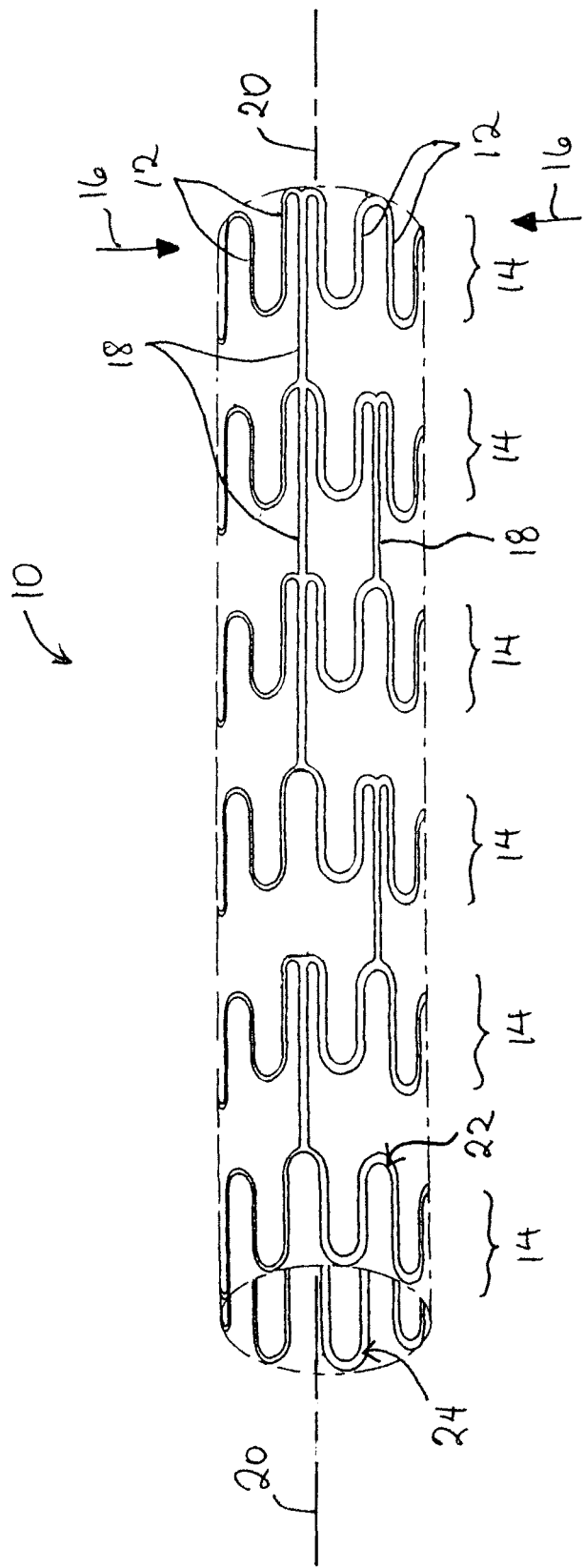
FIG. 1 is a perspective view of an exemplary endoprosthesis.
Figure 2:
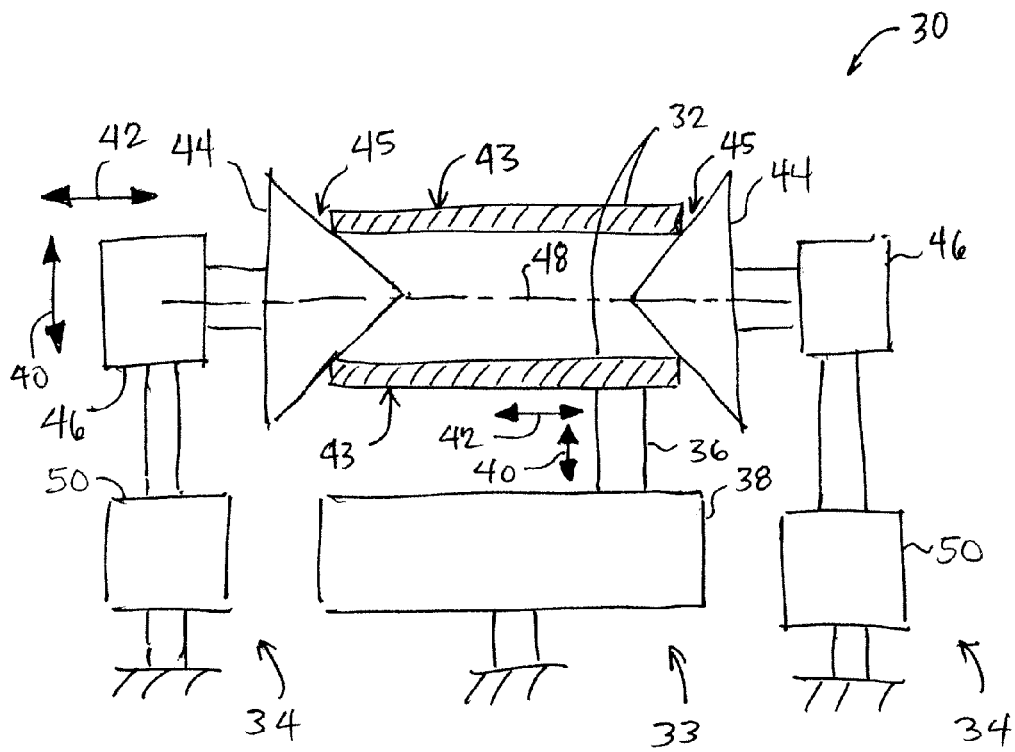
FIG. 2 is a diagrammatic side view of a system for coating an endoprosthesis, showing ends of the endoprosthesis engaged by a holding apparatus and showing a coating assembly applying a coating substance to an abluminal surface of the endoprosthesis.

Referring now in more detail to the exemplary drawings for purposes of illustrating embodiments of the invention, wherein like reference numerals designate corresponding or like elements among the several views, there is shown in FIG. 2 a system 30 for coating an endoprosthesis 32. The system 30 includes a coating assembly 33 for applying a coating substance to the endoprosthesis 32 and further includes holding assemblies 34 for holding the endoprosthesis in relation to the coating assembly. The coating assembly 33 includes an applicator 36 and a translation device 38 for translating the applicator in a radial direction 40 and an axial direction 42 relative to the endoprosthesis 32 and holding assemblies 34.

The applicator 36 carries the coating substance from a fluid reservoir or source to an abluminal surface 43 of the endoprosthesis 32. In some embodiments, a fluid conduit extends through the applicator 36 and terminates at an uppermost tip of the applicator. The fluid conduit delivers the coating substance so as to form an accumulation of the coating substance at the tip.

The holding assemblies 34 are adapted to move the endoprosthesis 32 into contact with the coating substance on the uppermost tip of applicator 36 so that the abluminal surface 43, but not the luminal surface 45, becomes coated with the coating substance. The holding assemblies 34 include holding members 44 having conical contacting surfaces 45 for example. The contacting surfaces 45 engage opposite ends of the endoprosthesis 32. The holding assemblies 34 also include rotating devices 46 coupled to the holding members 44. The contacting surfaces 45 are tapered or cone shaped so that they touch only the edges of the endoprosthesis 32, thereby avoiding or minimizing disturbance of any previously applied coating on the endoprosthesis 32. The rotating devices 46 are adapted to rotate the endoprosthesis 32 relative to the coating assembly 33. Specifically, the rotating devices 46 rotate the endoprosthesis 32 about the central axis 48 of the endoprosthesis. Each of the holding assemblies 34 also includes translation devices 50 for translating the contacting members 44 and the endoprosthesis 32 in radial directions 40 and axial directions 42 relative to the applicator 36. The rotating devices 46 and the translation devices 38, 50 may include without limitation motors, solenoids, gears, belts, rails and manually operated cranks. The rotating devices 46 and the translation devices 38, 50 allow for selective coating of the abluminal surface 43 of the endoprosthesis 32 as explained below.

In other embodiments, in which a temporarily implantable balloon is to be coated, holding assemblies are adapted to position the balloon above a coating applicator. The balloon can be part of a balloon catheter used in non-stenting angioplasty or part of a stent delivery system used to position and deploy a stent within a patient. The holding assemblies may include clamps, collets, and other devices for rotatably holding ends of the balloon or for rotatably holding a catheter to which the balloon is attached.

Figure 3:
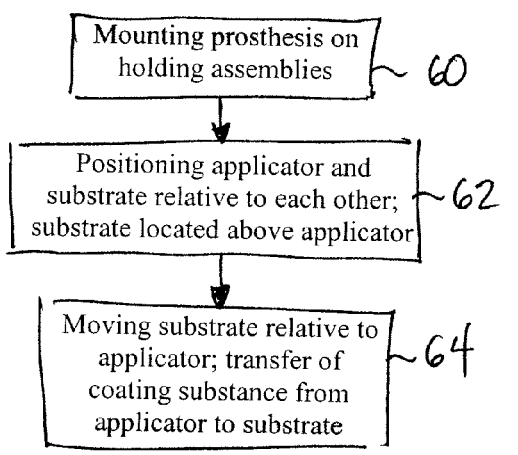
FIG. 3 is a flow diagram of a method for coating an endoprosthesis.

FIG. 3 shows an embodiment of a method in accordance with aspects of the invention. Although the method will be described in connection with the system 30 of FIG. 2, it will be appreciated that other coating systems may be used to implement the method for permanently and temporarily implanted endoprostheses. The method includes mounting 60 the endoprosthesis 32 on the holding assemblies 34. To mount the endoprosthesis 32, the holding members 44 can be pulled axially apart from each other so that the central axis 48 of the endoprosthesis can be aligned with center of the holding members. After the alignment, the holding members 44 can be axially translated closer to each other until they engage edges of the endoprosthesis 32.

The method further includes positioning 62 the coating applicator 36 and a substrate of the endoprosthesis 10 relative to each other so that the substrate is located above and in contact with the coating substance on the applicator. As used herein, "substrate" refers to a portion of the endoprosthesis 10 that is intended to be coated. In FIG. 2, the substrate is a portion of the abluminal surface 43 of the endoprosthesis. The abluminal surface may already have a film or coating layer already applied to it, in which case, the coating substance on the applicator is applied on top of the previously applied coating layer. In other embodiments, the substrate can be a portion of the luminal surface of an endoprosthesis.

The positioning 62 of FIG. 3 may include raising the applicator 36 toward the substrate and/or lowering the substrate toward the applicator 36 by activating one or a combination of the translation devices 38, 50. A controller in communication with the translation devices 38, 50 may be used to transmit electrical, electromagnetic, or electromechanical signals for activating the translation devices.

Still referring to FIG. 3, the method further includes moving 64 the substrate relative to the applicator 36 while the substrate is in contact with the coating substance on the applicator. Such movement may include any one or a combination of rotating the substrate about the central axis 48 of the endoprosthesis 32 and translating the substrate along the axial direction 42. At certain times during such movement, the substrate and applicator 36 may be separated from each other to prevent coating certain portions of the abluminal surface 43. In this way, it is possible to coat only selected portions of the abluminal surface 43. For example, a greater amount or concentration of the coating substance may be applied toward the middle of the endoprosthesis 32 as compared to the ends. As another example, a greater amount or concentration of the coating substance may be applied to half of the circumference of the endoprosthesis 32 to form a "half-pipe" distribution of the coating substance.

Figure 4:
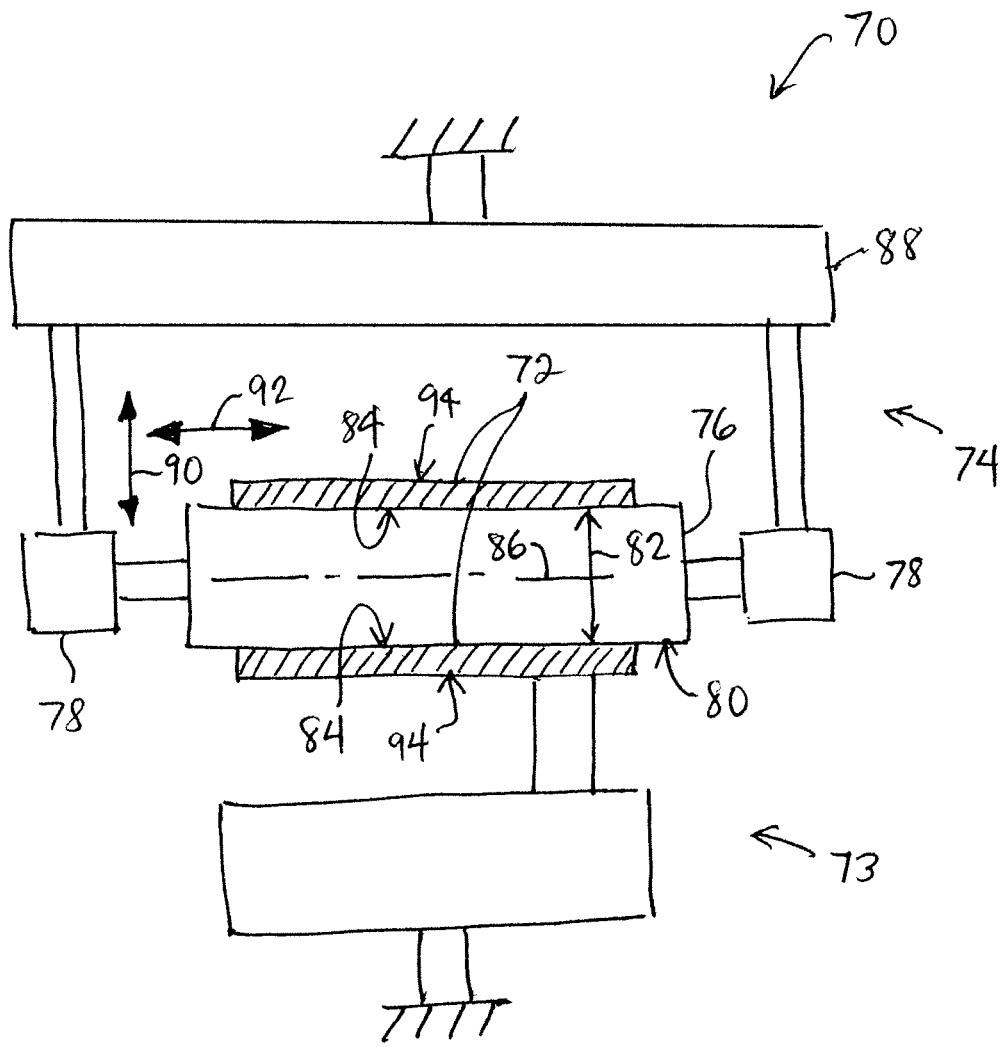
FIG. 4 is a diagrammatic side view of a system for coating an endoprosthesis, showing a holding assembly engaging a luminal surface of the endoprosthesis and showing a coating assembly applying a coating substance to an abluminal surface of the endoprosthesis.

In FIG. 4 there is shown another a system 70 for coating an endoprosthesis 72. The system 70 includes a coating assembly 73 for applying a coating substance to the endoprosthesis 72 and further includes a holding assembly 74 for holding the endoprosthesis in relation to the coating assembly.

The holding assembly 74 includes a cylindrical holding member 76 extending through the center of the endoprosthesis 72 and further includes rotation devices 78 coupled to the holding member 76. The holding member 76 has a cylindrical contacting surface 80 having an outer diameter 82 that corresponds to the inner diameter of a luminal surface 84 of the endoprosthesis 72. The contacting surface 80 engages the luminal surfaces 84 so that the endoprosthesis 72 moves with the holding member 76. Examples of a suitable holding member include but are not limited to mandrels, tubes, rods, catheters, and inflatable balloons. The rotation devices 78 are adapted to rotate the holding member 76 and the endoprosthesis 72 relative to the coating assembly 73. When the holding member 76 is rotated, the endoprosthesis 72 rotates about the central axis 86 of the endoprosthesis. The holding assembly 74 also includes a translation device 88 for translating the holding member 76 and the endoprosthesis 72 in radial directions 90 and axial directions 92 relative to coating assembly 73. The rotation devices 78 and the translation device 88 allow for selective coating of the abluminal surface 94 of the endoprosthesis 72.

In other embodiments, the holding assembly 74 may include clamps and/or collets adapted to engage an end segment of the endoprosthesis 72.

In FIGS. 5 and 6, a system 100 for coating an endoprosthesis 102 includes a coating assembly 103 for applying a coating substance to the endoprosthesis 102. The system 100 further includes holding assemblies 104 for holding the endoprosthesis 102 in relation to the coating assembly 103. The coating assembly 103 includes a coating applicator 106 sized to fit inside the endoprosthesis 102. The coating assembly 103 also includes a translation device 108 for translating the applicator in radial directions 110 and axial directions 112 relative to the endoprosthesis 102 and the holding assemblies 104. The applicator 106 carries the coating substance from a fluid reservoir or supply conduit to a luminal surface 113 of the endoprosthesis 102.

The holding assemblies 104 include cylindrical holding members 114 having cylindrical contacting surfaces 115 that engage and support an abluminal surface 116 of the endoprosthesis 102. The holding assemblies 104 further include rotating devices 118 coupled to the holding members 114. The rotating devices 118 rotate the holding members 114 and thereby rotate the endoprosthesis 102 about the central axis 120 of the endoprosthesis 102. Each of the holding assemblies 104 also includes a translation device 122 for translating the holding members 114 and the endoprosthesis 102 radial directions 110 and axial directions 112 relative to the applicator 106. In FIG. 6, the endoprosthesis 102 has been axially translated from a first position (depicted in broken lines) to a second position (depicted in solid lines) away from the applicator 106.

The rotating devices 118 and the translation devices 108, 122 may include without limitation motors, solenoids, gears, belts, rails and manually operated cranks. The rotating devices 118 and the translation devices 108, 122 allow for selective coating of the luminal surface 113 of the endoprosthesis 102.

In other embodiments, additional cylindrical holding members 114 may be implemented.

Figure 7:
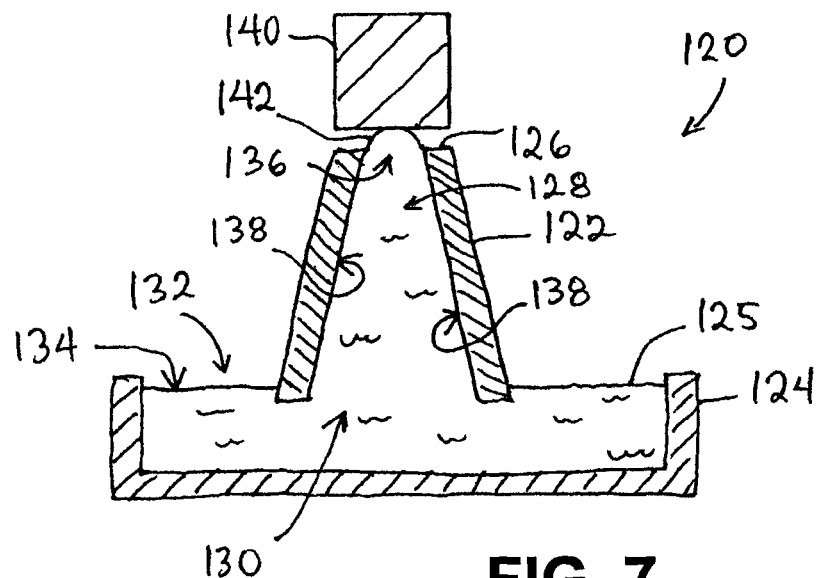
FIG. 7 is a diagrammatic cross-sectional view of a coating assembly, showing a tubular applicator having a tip carrying a convex meniscus of a coating substance in contact with a substrate of an endoprosthesis.

Referring next to FIG. 7, there is shown a coating assembly 120 that may be used with a system for coating an endoprosthesis, such as for example the systems illustrated in FIGS. 2, 4, 5 and 6. The coating assembly 120 includes an applicator 122 and an open container 124 carrying a pool of liquid coating substance 125. The applicator 122 includes an uppermost tip 126, an internal tube 128 capable the carrying a liquid coating substance vertically to the tip by capillary or wicking action. The tube 128 has an inlet 130 located at a bottommost tip 131 of the applicator 122. The inlet 130 is located within an opening 132 of the container 124 and submerged below or in contact with the surface 134 of the liquid coating substance 125. The tube 128 also has an outlet 136 at the uppermost tip 126 and interior surfaces 138 that are closer to each other at the outlet 136 than at the inlet 130.

The interior surfaces 138 may include curved portions that define a tapered interior space that is conical in shape. Alternatively or additionally, the interior surfaces 138 may include flat or planar portions that define an inverted V-shaped space in the tube 128.

The size of the inlet 130, size of the outlet 136, and vertical distance between the outlet 136 and the surface 134 of the coating substance is carefully selected so that the coating substance 125 is drawn up to the tip 126 by capillary action or wicking action, preferably without any assistance from a pump, at a sufficient rate to allow for transfer of the coating substance 125 to a substrate 140. In some embodiments, the size of the inlet 130 is larger than the size of the outlet 136. Preferably, though not necessarily, the material of the interior surfaces 138, at a region adjacent and/or below the uppermost tip 126, is selected to ensure that the coating substance forms a convex meniscus 142 above the uppermost tip 126. Generally, a liquid may form a convex meniscus having a shape somewhat like an inverted U-shape when molecules of the liquid have a stronger attraction to each other than to a tube. With the convex meniscus 142 of the coating substance 125 extending above the tip 126 of the applicator 122, the substrate 140 can be coated without making contact with the applicator 122, thereby reducing the possibility of damaging the substrate base material or coating layer previously applied to the substrate base material.

In other embodiments, a pump is implemented to assist with moving the coating substance 125 vertically to the uppermost tip 126. The pump can be used to create a consistent upward force or pressure on the coating substance 125 within the tube 128 so as to create the convex meniscus 142 or bubble at the uppermost tip 126.

When the substrate 140 has a sufficient affinity for the coating substance 125, the substrate 140 will "pull" or attract the coating substance 125 onto the substrate surface in a manner analogous to some extent to a dry sponge in contact with water. In such a case, the pump can be used to prime the coating process by initially bringing the coating substance 125 into contact with the substrate 140. After the coating substance 125 and substrate 140 make contact, capillary action will continue to draw the coating substance onto the surface of the substrate without use of the pump. When the substrate 140 and coating substance 125 have a lower affinity for each other, the pump can be used to continuously push the coating substance upward onto the surface of the substrate.

While the substrate 140 is in contact with the coating substance 125 at the uppermost tip 126, the substrate can be rotated or translated axially so as to transfer the coating substance from the uppermost tip to the substrate 140. During such transfer, the coating substance 125 at the uppermost tip 126 is continuously replaced by additional coating substance 125 in the container 124. Movement of the additional coating substance upwards to the uppermost tip 26 can be by active pumping using a pump and/or by capillary action.

The outlet 136 can be in the shape of a circle or an elongated slot. When the endoprosthesis to be coated is a stent, the size of the outlet 136 can be selected to allow one strut, one ring, an entire side of an endoprosthesis, any length between the three, to be coated during rotation and/or axial translation of the endoprosthesis.

In other embodiments, the inner radius defining the interior surfaces 138 is constant so that inlet 130 and outlet 136 have the same size. The capillary height is the vertical distance a liquid would rise within the applicator 122 above the surface 134 of the coating substance in the container 124 by means of capillary action. The capillary height can be determined by the formula:

$$H = 2\gamma \cos \theta / (\rho g r)$$

where $\gamma$ is the liquid-air surface tension,
$\theta$ is the contact angle between the liquid and vertical walls within the tube,
$\rho$ is the density of the liquid,
$g$ is gravitational acceleration,
$r$ is the inner radius of the applicator.

The contact angle is a function of the intermolecular forces within the coating substance 125 and between the coating substance and the applicator 122. The intermolecular forces are influenced by the composition of the coating substance 125 and the surface material chosen for the applicator 122. There will be a smaller contact angle in cases where the coating substance 125 is attracted to the applicator surface material as compared to cases where the coating substance is less attracted to or repelled by the applicator material. Therefore, it is important to select the height, surface material, and/or inner radius of the applicator 122 to help ensure that a coating substance having a given density and surface tension reaches the uppermost tip 126 by means of capillary action.

Figure 8:
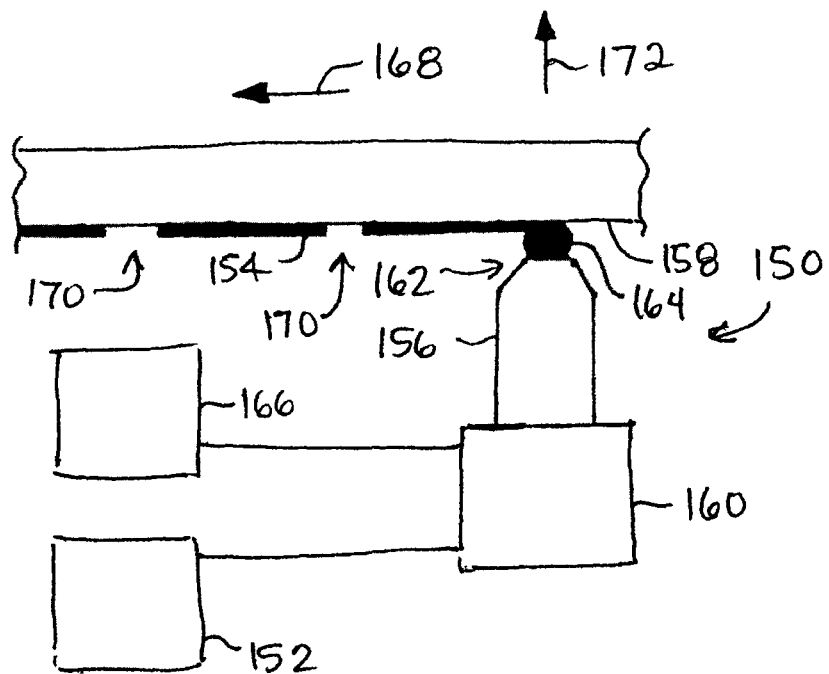
FIG. 8 is a diagrammatic detailed view of a coating assembly, showing a pump delivering a coating substance from a source to a die and showing a bead of the coating substance formed at the tip of the die.

FIG. 8 shows another coating assembly 150 that may be used with the coating systems of FIGS. 2, 4, 5 and 6 and other systems. The coating assembly 150 includes a reservoir 152 holding a coating substance 154, an applicator die 156 through which the coating substance is extruded and delivered to a substrate 158, and a pump 160 for moving the coating substance from the reservoir to an outlet 162 of the die. Preferably, though not necessarily, the pump 160 is operated to move the coating substance 154 at a flow rate such that a bead 164 of the coating substance is maintained above the outlet 162 of the die 156. With the bead 164 extending above the outlet 162, the substrate 158 can optionally be coated without making contact with the die 154, thereby reducing the possibility of damaging the substrate base material or coating layer previously applied to the substrate base material. The pump 160 may be operated to move the coating substance 154 at a flow rate determined by a controller 166 based at least on the rate of movement of the substrate 158 relative to the die 154.

The substrate 158 in FIG. 8 is translated in an axial direction 168 relative to the die 156 to transfer the coating substance 154 from the die to the substrate. During axial translation, the pump 166 continually replenishes the coating substance 154 in the bead 164. Breaks or gaps 170 in the coating are created by moving the substrate in a radial direction 172 away from the die 156. In other embodiments, the substrate is rotated or axially translated while it is rotated.

Figure 9:
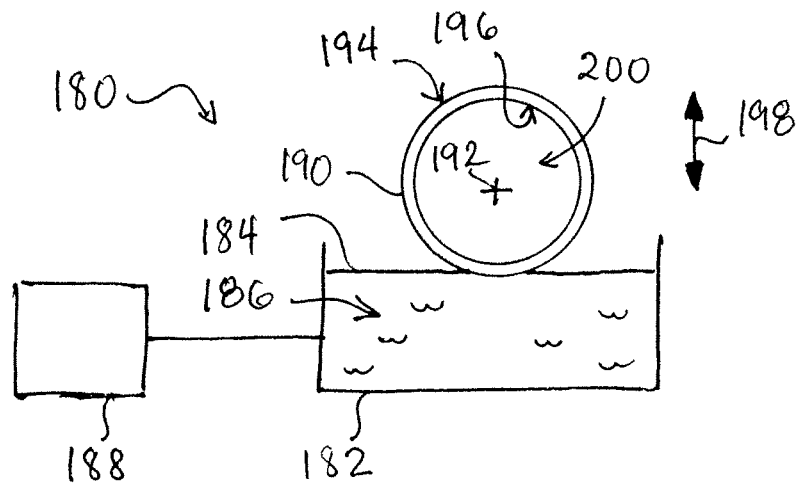
FIG. 9 is a diagrammatic end view of another coating assembly, showing an abluminal surface of an endoprosthesis skipping across the surface of a pool of coating substance.

FIG. 9 shows an exemplary coating assembly 180 that may be implemented with systems for coating an endoprosthesis. The coating assembly 180 includes an applicator 182 carrying an exposed pool 184 of a liquid coating substance 186. Optionally, the pool is connected to a supply 188 for providing additional liquid coating substance.

In operation, an endoprosthesis 190 is positioned above the applicator 182 and brought into contact with the exposed pool 184. The endoprosthesis 190 is coated by rotating it about its central axis 192 and/or translating it in an axial direction parallel or substantially parallel to the central axis. When the endoprosthesis to be coated is a stent, the size of the exposed pool 184 can be selected to allow one strut, one ring, or an entire side of the endoprosthesis to be coated during rotation and/or translation. In the illustrated embodiment, the applicator 182 is located outside of the endoprosthesis 190 to allow for selective coating of an abluminal surface 194 of the endoprosthesis. Coating of a luminal surface 196, and optionally side walls between the abluminal and luminal surfaces, is avoided or minimized by controlling the radial position of the endoprosthesis 190 relative to the surface of the pool 184. During rotation and/or translation, the abluminal surface 194 skips across the exposed surface of the pool 184. Coating of portions of the abluminal surface 194 may be avoided by separating the endoprosthesis 190 from the pool 184, which can be done by moving either one or both of the endoprosthesis 190 and the pool 184 in a radial direction 198.

In other embodiments, the applicator 182 can be sized to fit inside the lumen 200 of the endoprosthesis 190 to allow for selective coating of the luminal surface 196. To facilitate coating the luminal surface 196, the supply 188 may be controlled to maintain a raised bead of the coating substance 186 slightly above the walls of the container 182.

Figure 10:
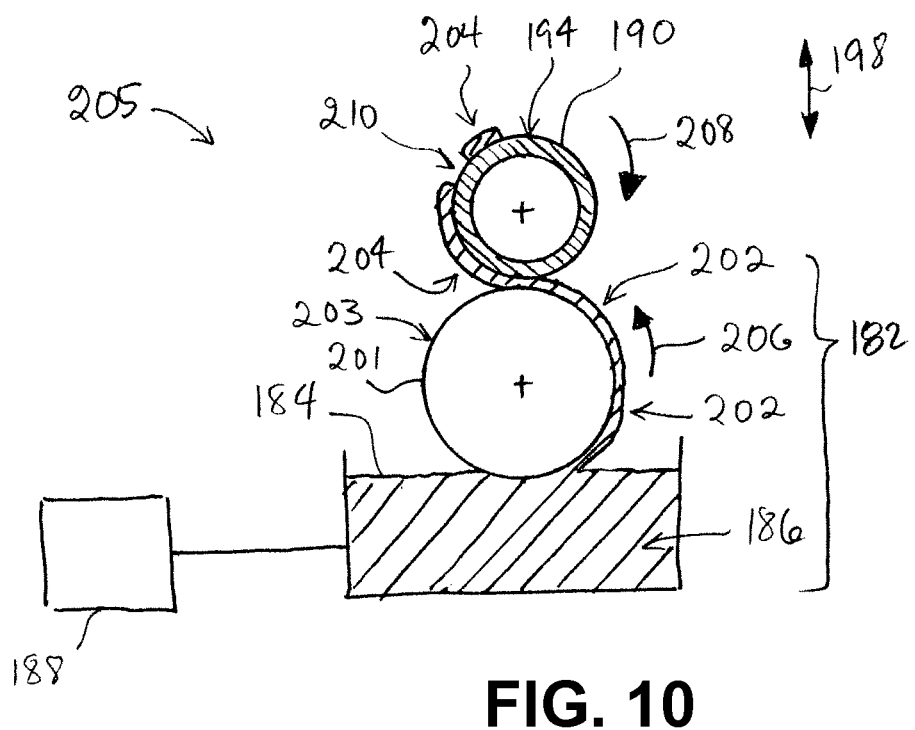
FIG. 10 is an end view of a coating assembly, showing an abluminal surface of a prosthesis contacting or touching a coating fluid that is transferred from a roller in contact with a coating fluid bath.

FIG. 10 shows an embodiment of a coating assembly 205 that may be implemented with systems for coating an endoprosthesis. The coating assembly 205 includes an applicator 182 carrying an exposed pool 184 of a liquid coating substance 186. The applicator 182 includes a circular transfer roller 201 in contact with the exposed pool 184. When the transfer roller rotates in a first direction 206, the roller picks up the liquid coating substance 186. The coating substance 186 is deposited as a transfer film or layer 202 on an outer surface 203 of the transfer roller 201. An abluminal surface 194 of a prosthesis 190 contacts the transfer layer 202 on the transfer roller 201. When the prosthesis 190 rotates in a second direction 208, the prosthesis obtains a coating layer 204 of the coating substance 186 on its abluminal surface 194.

Selective coating can be achieved by separating the prosthesis 190 and transfer roller 201 from each other by translation in radial directions 198. In this way, selected portions 210 of the abluminal surface 194 can be free of the coating layer 204. When the endoprosthesis to be coated is a stent, the axial dimension of the transfer roller 203 can be selected to allow one strut, one ring, an entire side of the stent, and any length between the three, to be coated during rotation.

In other embodiments, the prosthesis 194 is translated axially relative to the rotating transfer roller 203 in order to obtain the coating layer 204 on its abluminal surface 194.

It will be appreciated that the present invention encompasses any type of coating substance. Coating substances may include one or a combination of polymers, solvents, and beneficial agents. Polymers include compounds that are the product of a polymerization reaction and are inclusive of homopolymers, co-polymers, terpolymers etc., including random, alternating, block, and graft variations thereof "Solvent" is defined as a liquid substance or composition which is compatible with the polymer and is capable of dissolving the polymer at the concentration desired in the composition. Beneficial agents encompass active ingredients capable of exerting a therapeutic or prophylactic effect. Examples of such active ingredients include angiogenic, antiproliferative, antineoplastic, antiinflammatory, antiplatelet, anticoagulant, antifibrin, antithrombin, antimitotic, antibiotic, and antioxidant substances as well as combinations thereof. Beneficial agents also encompass proteins, hormones, genes, plasmids, cell-signaling agents, interleukins, etc.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method of coating an endoprosthesis, comprising:
   forming an accumulation of a coating substance on an uppermost tip of a fluid conduit, the accumulation extending above the tip;
   bringing the accumulation on the tip and a portion of an endoprosthesis into contact with each other, the portion of the endoprosthesis located above the accumulation; and
   translating or rotating the endoprosthesis relative to the tip while the accumulation on the tip and the endoprosthesis are in contact with each other, thereby transferring the coating substance from the tip to the endoprosthesis.

2. The method of claim 1, further comprising maintaining the accumulation on the tip while translating or rotating the endoprosthesis relative to the tip.

3. The method of claim 1, wherein the accumulation is maintained by capillary flow or wicking action through the fluid conduit.

4. A method of coating an endoprosthesis, comprising:
   positioning an applicator and a substrate of an endoprosthesis relative to each other so that the substrate is located above and in contact with a coating substance on the applicator; and
   moving the substrate relative to the applicator while the substrate is in contact with the coating substance on the applicator so that the coating substance is transferred from the applicator to the substrate, wherein the applicator includes a vertical tube for delivering the coating substance to an uppermost tip of the applicator, the vertical tube having an outlet at the tip, an inlet below the outlet, and interior surfaces that are closer to each other at the outlet than at the inlet.

5. The method of claim 4, wherein the applicator does not contact the substrate and the applicator includes a tube for delivering the coating substance to an aperture of the applicator.

6. The method of claim 5, further comprising delivering the coating substance to the aperture of the applicator by capillary action or wicking action within the applicator.

7. The method of claim 5, further comprising forming a convex meniscus of the coating substance above the aperture of the applicator.

8. The method of claim 5, further comprising using a pump to form a bead of the coating substance above the aperture of the applicator.

9. The method of claim 4, wherein the endoprosthesis is an implantable balloon and the substrate is an outer surface of the implantable balloon.

10. The method of claim 9, wherein the implantable balloon is an angioplasty balloon.

11. The method of claim 9, wherein the implantable balloon is part of a stent delivery system.

12. The method of claim 4, further comprising delivering the coating substance to the substrate by capillary action or wicking action within the applicator.

13. The method of claim 4, further comprising moving the coating substance through the applicator without a pump.

* * * * *